(12) United States Patent
Carvalio

(10) Patent No.: US 7,615,074 B2
(45) Date of Patent: Nov. 10, 2009

(54) METHOD AND APPARATUS FOR RECONSTRUCTIVE SURGERY

(76) Inventor: Edward Carvalio, 106 Homeport Dr., Ozona, FL (US) 34683

(*) Notice: Subject to any disclaimer, the term of this patent is extended or adjusted under 35 U.S.C. 154(b) by 638 days.

(21) Appl. No.: 11/211,340

(22) Filed: Aug. 25, 2005

(65) Prior Publication Data
US 2007/0050026 A1    Mar. 1, 2007

(51) Int. Cl.
*A61F 2/12* (2006.01)
*A61F 2/52* (2006.01)
*A61M 29/00* (2006.01)

(52) U.S. Cl. .................. 623/8; 623/7; 606/192

(58) Field of Classification Search .......... 623/7, 623/8
See application file for complete search history.

(56) References Cited

U.S. PATENT DOCUMENTS

| | | | |
|---|---|---|---|
| 2,636,182 A | 4/1953 | Freedman | |
| 3,852,833 A | 12/1974 | Koneke et al. | |
| 3,934,274 A | 1/1976 | Hartley, Jr. | |
| 4,205,401 A * | 6/1980 | Frisch | 623/8 |
| 4,433,440 A * | 2/1984 | Cohen | 623/8 |
| 4,605,412 A * | 8/1986 | LaForest et al. | 623/8 |
| 4,651,717 A * | 3/1987 | Jakubczak | 128/899 |
| 4,773,909 A * | 9/1988 | Chaglassian | 623/8 |
| 4,790,848 A | 12/1988 | Cronin | |
| 5,116,370 A * | 5/1992 | Foglietti | 623/8 |
| 5,146,933 A * | 9/1992 | Boyd | 128/899 |
| 5,147,398 A | 9/1992 | Lynn et al. | |
| 5,236,454 A * | 8/1993 | Miller | 623/8 |
| 5,356,429 A * | 10/1994 | Seare | 623/8 |
| 5,358,521 A * | 10/1994 | Shane | 623/8 |
| 5,447,535 A * | 9/1995 | Muller | 623/8 |
| 5,500,019 A | 3/1996 | Johnson et al. | |
| 6,228,116 B1 * | 5/2001 | Ledergerber | 623/8 |
| 6,537,318 B1 * | 3/2003 | Ita et al. | 623/11.11 |
| 6,755,861 B2 * | 6/2004 | Nakao | 623/8 |
| 6,875,233 B1 * | 4/2005 | Turner | 623/8 |
| 2002/0038147 A1 | 3/2002 | Miller, III | |

* cited by examiner

*Primary Examiner*—Thomas J Sweet
*Assistant Examiner*—Andrew Iwamaye
(74) *Attorney, Agent, or Firm*—Larson & Larson, P.A.; Frank Liebenow

(57) ABSTRACT

A method of biological reconstruction and a device having a major chamber or compartment in the form of the desired anatomy with a shaped chamber inside the main chamber flipped up and held in place by one or more inflatable piston chambers. The inflatable piston chambers selectively hold the shaped chamber and are pressurized in order to support the shape of the device upon implantation. Valves are provided to allow filling the major chamber, the shaped chamber and the piston chambers with a biologically compatible fluid.

26 Claims, 4 Drawing Sheets

METHOD AND APPARATUS FOR RECONSTRUCTIVE SURGERY

BACKGROUND OF THE INVENTION

1. Field of the Invention

This invention relates to a method for reshaping a portion of an organism through implantation of an expandable prosthesis and the prosthesis itself. This invention is particularly suitable for providing a female breast with a more desirable shape.

2. Description of the Related Art

For various reasons, including reconstructive surgery, implants have been used for many years to restore a natural size and shape to various parts of the anatomy, in particular to breasts. In particular, mammary implants are known in the prior art as evidenced in U.S. Pat. Nos. 2,636,182, 3,934,274, 4,605,412, 4,790,848 and 5,236,454.

Methods used in the past often resulted in an unnatural appearance. One prior method included a silicone sac filled with saline and placed beneath the pectoral muscle. This bag is usually shaped in the form of a breast, but, unfortunately, the saline acts in accordance with the laws of fluids and gravity and, sometimes, over time as a scar forms around the bag (forming a capsule), it distributes itself into a spherical shape, resulting in an unnatural appearance of a ball placed beneath the skin rather than the shape of a natural breast. Another problem with prior attempts to reconstruct a natural shape is maintaining projection. Due to the redistribution of fluids within the sac, the top section of the prosthesis loses fluid, creating a flat or concave appearance on the top area of the breast, when a full, rounded shape is desired.

U.S. Pat. No. 6,755,861 to Nakao describes a multi-chamber implantable device and is hereby incorporated by reference. The individual chambers are pressurized under computer control to control the shape upon implantation. This device has many smaller chambers, each having an interface to each other and the outer shell, producing an uneven feel and surface appearance.

What is needed is an implant that will support the desired shape with an even surface texture and with a dependable shape that lasts. What is also needed is an implant that works well to lift minimally or moderately droopy breasts and one that helps prevent later-life drooping when implanted behind a youthful breast.

SUMMARY OF THE INVENTION

In one embodiment, a breast implant is disclosed including a major chamber with a back wall and a shaped chamber located within an upper portion of the major chamber. At least two piston chambers are within the major chamber and are configured to flip up and hold the shaped chamber in place. A valve is associated with each chamber for admitting a biologically compatible fluid into the chamber with which it is associated.

In another embodiment, a breast implant is disclosed including a major chamber having a back wall, the back wall with a top end configured to be positioned in the direction of a head of the person (cephalad) and a bottom end configured to be positioned in the direction of a waist of the person (caudal). Within the major chamber is a shaped chamber positioned towards the top end of the major chamber with a first end affixed to the back wall of the major chamber. There is at least one piston chamber within the major chamber configured to flip and hold the shaped chamber in place. A proximal end of the at least one piston chamber is affixed to a second end of the shaped chamber and a distal end of the at least one piston chamber is affixed to the back wall substantially near the bottom end. A valve is associated with each chamber for admitting fluid into the chamber with which it is associated.

In another embodiment, a method of breast implantation is disclosed including inserting a breast implant through an incision in the breast, the breast implant having a major chamber with a back wall. Within an upper portion of the major chamber is a shaped chamber. There are at least two piston chambers within the major chamber for flipping and holding the shaped chamber in place. A valve is associated with each chamber for admitting a biologically compatible fluid into each chamber with which it is associated. Next, positioning the breast implant so the shaped chamber is positioned toward the top portion of the breast and then filling the major chamber and the shaped chamber with the biologically compatible fluid. Finally, inserting the biologically compatible fluid into the at least two piston chambers.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
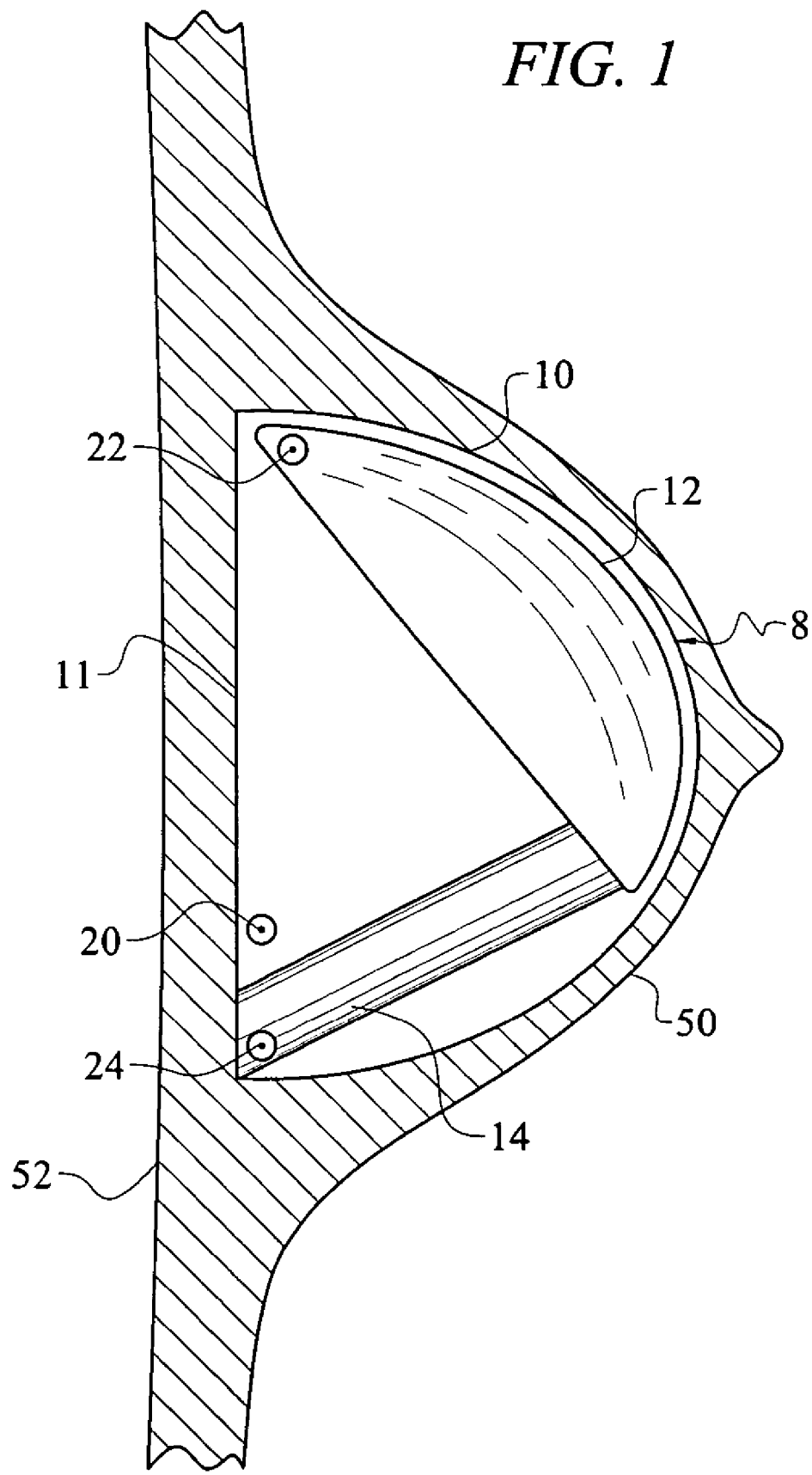
FIG. 1 is a schematic cross-sectional view of a breast prosthesis in accordance with the present invention.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a schematic side elevational view of a breast prosthesis in accordance with the present invention will be described. The implant 8 has been surgically inserted under or behind the breast 50, supported in the rear by other biological matter 52 such as muscle. The implant 8 is made from a soft, bendable, biologically compatible material such as silicone or silica. The implant 8 is made in various sizes to accommodate variations in breast sizes and desired target breast sizes and shapes. There are at least three chambers composed of this material. A major chamber 10 is a sac encapsulating the entire implant 8 and all other chambers. A valve 20 in the outer surface of the major chamber 10 allows introduction of a biologically compatible fluid such as saline or a soy-based solution. Within the major chamber 10 is a shaped chamber 12. The shaped chamber 12 is positioned in an upper portion of the major chamber 10. The shaped chamber 12 is attached to the top of the back wall 11 of the major chamber 10, the top being the end of the back wall 11 that is positioned substantially in the direction of the person's head (cephalad). A valve 22 is provided for filling the shaped chamber with a biologically compatible fluid. The valve 22 interfaces with a surface of the major chamber 10 such that fluid can be injected into the shaped chamber without violating the integrity of the major chamber 10. In some embodiments, the shaped chamber 12 is attached to the back wall 11 of the major chamber 10 by the valve 22. All valves are on a surface of the implant 8 that is well within the body and in a location that permits filling the sacs from the outside after the implant 8 is inserted under the patient's breast. In some embodiments, the shaped chamber 12 is in the shape of a crescent-dome, a dome or a half-moon.

Supporting the shaped chamber 12 is at least one sac in the shape of a piston 14, preferably two pistons 14. One end of the piston 14 is attached to the underside of the shaped chamber 12 near a distal end of its back surface (towards the front of the breast 50) and the opposite end is attached to the back wall 11 of the major chamber 10 at a point near the bottom of the back wall 11. Valves 24 are provided for filling the piston(s) 14 with a biologically compatible fluid. The valves 24 interface with a surface of the major chamber 10 such that fluid can be injected into the piston(s) 14 without violating the integrity of the major chamber 10. In some embodiments, the piston(s) 14 are attached to the back wall 11 of the major chamber 10 by the valve 24 while in other embodiments, the piston(s) 14 are affixed or are part of the back wall 11 of the major chamber 10. The shape of the piston(s) 14 is not significant; it only needs to provide support to the shaped chamber 12. Furthermore, in some embodiments some or all of the chambers or sacs are pre-filled with a volume of biologically compatible fluid.

In most procedures, the implant 8 is inserted under the breast through a small incision made in a location medically recognized as an acceptable incision site for a breast augmentation such as in an existing scar, beneath the breast or around the lower portion of the areola. Once inserted and positioned so that the shaped chamber 12 is substantially in an upward position, the chambers are filled with a biologically compatible solution. The shaped chamber 12 is flipped-up and held in the upper portion of the breast by the piston(s) 14, providing a superior lift to the overlying breast. The outer, major chamber 10 reduces ones ability to feel the other chambers within the breasts. The present invention works equally well on all types of breasts, but is very well suited for mildly droopy or moderately droopy breasts. Furthermore, the present invention works well on youthful breasts, possibly preventing future drooping with age.

Figure 2:
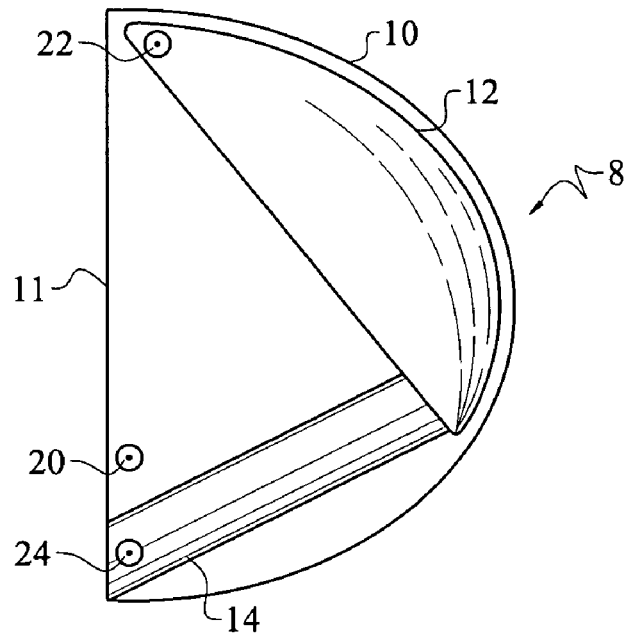
FIG. 2 is a cross-sectional view of the breast prosthesis of FIG. 1.

Referring to FIG. 2, a cross-sectional view of the breast prosthesis of FIG. 1 will be described. There are at least three chambers. A major chamber 10 is a sac encapsulating the entire implant 8 and all other chambers. A valve 20 in the outer surface of the major chamber 10 allows introduction of a biologically compatible fluid such as saline or soy-based solution. Within the major chamber 10 is a shaped chamber 12. The shaped chamber 12 is positioned in an upper portion of the major chamber 10. The shaped chamber 12 is attached to a top inside surface of the major chamber 10, the top being the end of the back wall 11 that is positioned substantially in the direction of the patient's head when implanted (cephalad). A valve 22 is provided for filling the shaped chamber with a biologically compatible fluid. The valve 22 interfaces with a surface of the major chamber 10 such that fluid can be injected into the shaped chamber without violating the integrity of the major chamber 10. In some embodiments, the shaped chamber 12 is attached to a surface of the major chamber 10 by the valve 22. All valves are on a surface of the implant 8 that is well within the body and in a location that permits filling the sacs from the outside after the implant 8 is inserted under the patient's breast. In some embodiments, the shaped chamber 12 is in the shape of a crescent-dome, a dome or a half-moon.

Supporting the shaped chamber 12 is at least one sac in the shape of a piston 14. One end of the piston 14 is attached to the shaped chamber 12 near a distal end of its back surface and the opposite end is attached to an inside surface of the major chamber 10 at a point near the bottom of the back wall 11 (caudal). Valves 24 are provided for filling the piston(s) 14 with a biologically compatible fluid. The valves 24 interface with a surface of the major chamber 10 such that fluid can be injected into the piston(s) 14 without violating the integrity of the major chamber 10. In some embodiments, the piston(s) 14 are attached to the back wall 11 of the major chamber 10 by the valve 24 while in other embodiments, the piston(s) 14 are affixed or are part of an inside surface of the major chamber 10.

Figure 3:
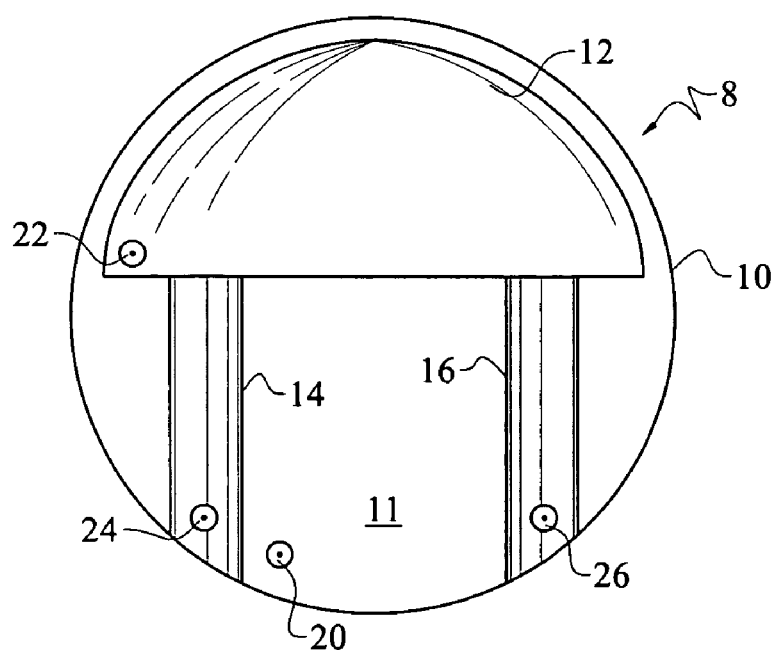
FIG. 3 is a schematic front elevational view of the prosthesis of FIG. 1.

Referring to FIG. 3, a schematic front elevational view of the prosthesis of FIG. 1 will be described. In this example, there are four chambers. A major chamber 10 is a sac encapsulating the entire implant 8 and all other chambers. A valve 20 in the outer surface of the major chamber 10 allows introduction of a biologically compatible fluid such as saline or soy-based solution. Within the major chamber 10 is a shaped chamber 12. The shaped chamber 12 is positioned in an upper portion of the major chamber 10. The shaped chamber 12 is attached to a top inside surface of the major chamber 10, the top being the end of the back wall 11 that is positioned substantially in the direction of the patient's head when implanted (cephalad). A valve 22 is provided for filling the shaped chamber with a biologically compatible fluid. The valve 22 interfaces with a surface of the major chamber 10 such that fluid can be injected into the shaped chamber without violating the integrity of the major chamber 10. In some embodiments, the shaped chamber 12 is attached to the back wall 11 of the major chamber 10 by the valve 22. All valves are on a surface of the implant 8 that is well within the body and in a location that permits filling the sacs from the outside after the implant 8 is inserted under the patient's breast. In some embodiments, the shaped chamber 12 is in the shape of a crescent-dome, a dome or a half-moon.

Supporting the shaped chamber 12 are two sacs in the shape of a piston 14/16. One end of the pistons 14/16 is attached to the shaped chamber 12 near a distal end of its back surface and the opposite end is attached to the back wall 11 or other inside surface of the major chamber 10 at a point near the bottom of the back wall 11 (caudal). Valves 24/26 are provided for filling the piston 14/16 with a biologically compatible fluid. The valves 24/26 interface with a surface of the major chamber 10 such that fluid can be injected into the piston 14/16 without violating the integrity of the major chamber 10. In some embodiments, the piston 14/16 are attached to the back wall 11 of the major chamber 10 by the valve 24 while in other embodiments, the piston 14 are affixed or are part of an inside surface or the back wall 11 of the major chamber 10.

Figure 4:
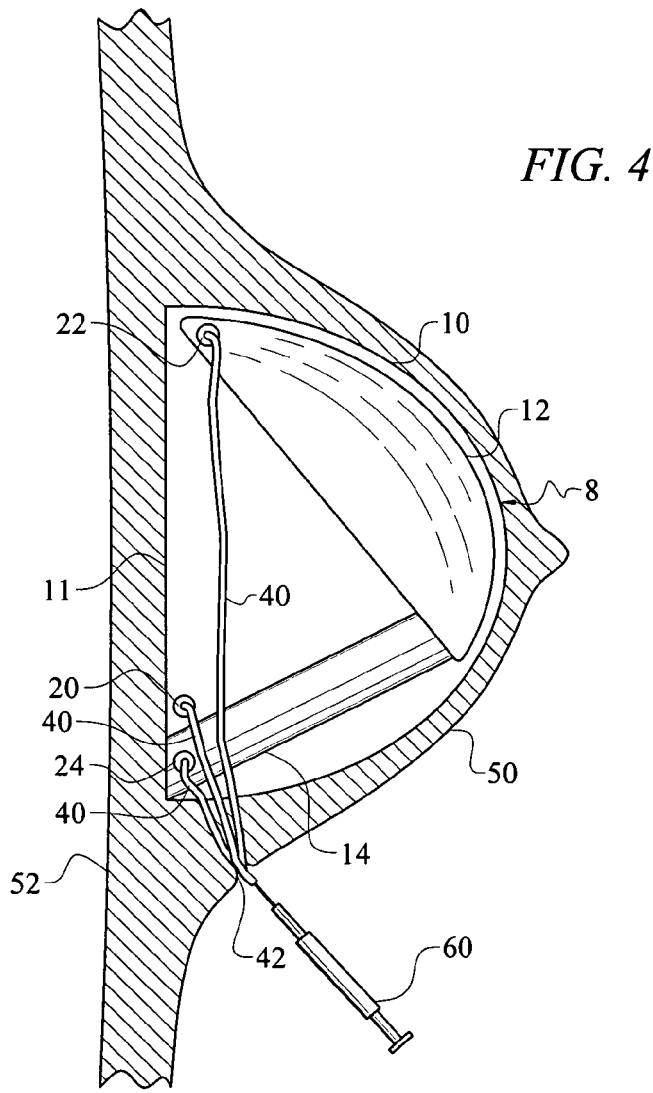
FIG. 4 is a schematic side elevational view of a breast prosthesis of FIG. 1 showing the injection of a fluid.

Referring to FIG. 4, a schematic side elevational view of a breast prosthesis of FIG. 1 showing the injection of a fluid will be described. The implant 8 has been surgically inserted beneath the breast 50 through an incision 42 and is supported in the rear by other biological matter 52 such as muscle. The major chamber 10 is a sac encapsulating the entire implant 8 and all other chambers. A valve 20 in the outer surface of the major chamber 10 allows introduction of a biologically compatible fluid through an easy-to-disconnect tube 40 and may be filled with a syringe 60 or other pressurizing device. After filling each chamber, the tubes 40 are pulled off and away from their respective valve and discarded. Within the major chamber 10 is a shaped chamber 12. The shaped chamber 12 is positioned in an upper portion of the major chamber 10. The shaped chamber 12 is attached to an inside surface of the major chamber 10 near the top, the top being the end of the back wall 11 that is positioned substantially in the direction of the person's head (cephalad). A valve 22 allows introduction of a biologically compatible fluid by the easy-to-disconnect tube 40 and may be filled by a syringe 60 or other pressurizing device, then pulled off and away and discarded. The valve 22 interfaces with a surface of the major chamber 10 such that fluid can be injected into the shaped chamber without violating the integrity of the major chamber 10. In some embodiments, the shaped chamber 12 is attached to the back wall 11 of the major chamber 10 by the valve 22. All valves are on a surface of the implant 8 that is well within the body and in a location that permits filling the sacs from the easy-to-disconnect tubes 40 after the implant 8 is inserted into the patient's breast. In some embodiments, the shaped chamber 12 is in the shape of a crescent-dome, a dome or a half-moon.

Supporting the shaped chamber 12 is at least one sac in the shape of a piston 14. One end of the piston 14 is attached to the shaped chamber 12 near a distal end of the shaped chamber's 12 back surface (towards the front of the breast 50) and the opposite end is attached to the an inside surface or back wall 11 of the major chamber 10 at a point near the bottom of the back wall 11 (caudal). The valves 24 allow the introduction of a biologically compatible fluid through easy-to-disconnect tubes 40 using a syringe 60 or other pressurizing device. The valves 24 interface with a back wall 11 of the major chamber 10 such that fluid can be injected into the piston(s) 14 without violating the integrity of the major chamber 10. In some embodiments, the piston(s) 14 are attached to the back wall 11 of the major chamber 10 by the valves 24 while in other embodiments, the piston(s) 14 are affixed or are part of a lower inside surface or the back wall 11 of the major chamber 10.

In most procedures, the implant 8 is inserted beneath the breast through a small incision 42 made in a location medically recognized as an acceptable incision site for a breast augmentation such as in an existing scar, beneath the breast or around the lower portion of the areola. Once inserted and positioned so that the shaped chamber 12 is substantially in an upward position, the chambers are filled with a biologically compatible solution through easy-to-disconnect tubes using a syringe 60 or other pressurizing device. The shaped chamber 12 is flipped-up and held in the upper portion of the breast by the piston(s) 14, providing a superior lift to the overlying breast. The outer, major chamber 10 reduces ones ability to feel the other chambers within the breast.

Figure 5:
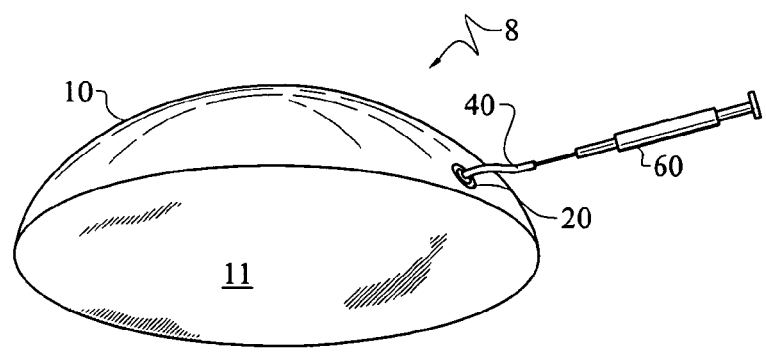
FIG. 5 is an isometric view of a breast prosthesis of FIG. 1 showing the injection of a fluid.

Referring to FIG. 5, an isometric view of a breast prosthesis of FIG. 1 showing the injection of a fluid will be described. The major chamber 10 is a sac encapsulating the entire implant 8 and all other chambers and has a back wall 11. A valve 20 in the outer surface of the major chamber 10 allows introduction of a biologically compatible fluid through an easy-to-disconnect tube using a syringe 60 or other pressurizing device.

Figure 6:
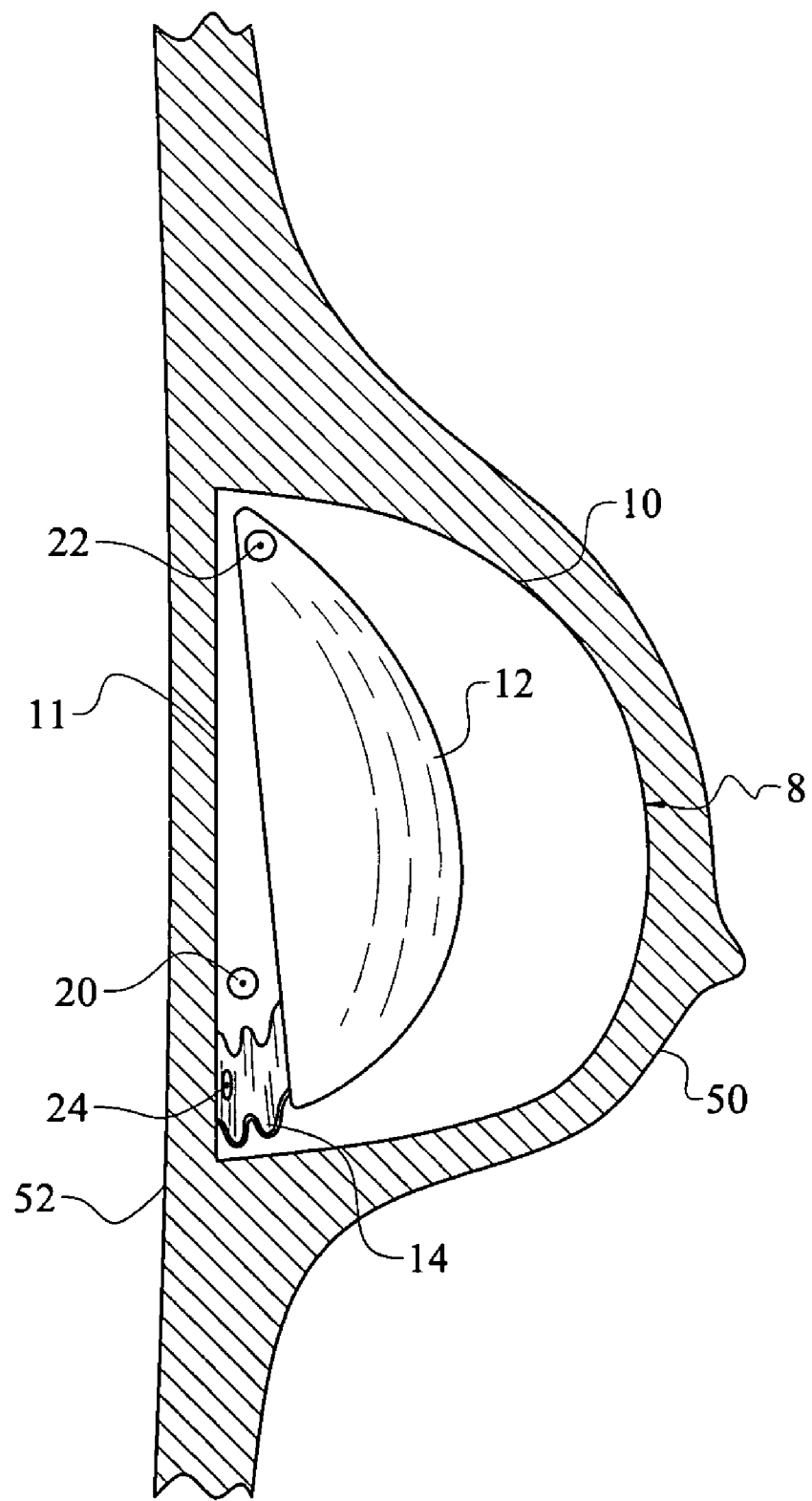
FIG. 6 is a cross-sectional view of the breast prosthesis of FIG. 1.

Referring to FIG. 6, a schematic side elevational view of a breast prosthesis in accordance with the present invention will be described. The implant 8 has been surgically inserted under or behind the breast 50, supported in the rear by other biological matter 52 such as muscle. There are at least three chambers composed of this material. A major chamber 10 is a sac encapsulating the entire implant 8 and all other chambers. A valve 20 in the outer surface of the major chamber 10 allows introduction of a biologically compatible fluid such as saline or a soy-based solution. Within the major chamber 10 is a shaped chamber 12. In this figure, the shaped chamber 12 is positioned in an unsupported position within the major chamber 10. The shaped chamber 12 is attached to the top of the back wall 11 of the major chamber 10, the top being the end of the back wall 11 that is positioned substantially in the direction of the person's head (cephalad). A valve 22 is provided for filling the shaped chamber with a biologically compatible fluid. The valve 22 interfaces with a surface of the major chamber 10 such that fluid can be injected into the shaped chamber without violating the integrity of the major chamber 10. In some embodiments, the shaped chamber 12 is attached to the back wall 11 of the major chamber 10 by the valve 22. All valves are on a surface of the implant 8 that is well within the body and in a location that permits filling the sacs from the outside after the implant 8 is inserted under the patient's breast. In some embodiments, the shaped chamber 12 is in the shape of a crescent-dome, a dome or a half-moon.

Supporting the shaped chamber 12 is at least one sac in the shape of a piston 14, preferably two pistons 14. In this figure, the piston 14 is yet to be filled with the biologically compatible fluid and is shown in its relaxed state, allowing insertion. One end of the piston 14 is attached to the underside of the shaped chamber 12 near a distal end of its back surface (towards the front of the breast 50) and the opposite end is attached to the back wall 11 of the major chamber 10 at a point near the bottom of the back wall 11. Valves 24 are provided for filling the piston(s) 14 with a biologically compatible fluid. The valves 24 interface with a surface of the major chamber 10 such that fluid can be injected into the piston(s) 14 without violating the integrity of the major chamber 10. In some embodiments, the piston(s) 14 are attached to the back wall 11 of the major chamber 10 by the valve 24 while in other embodiments, the piston(s) 14 are affixed or are part of the back wall 11 of the major chamber 10. The shape of the piston(s) 14 is not significant; it only needs to provide support to the shaped chamber 12. Furthermore, in some embodiments some or all of the chambers or sacs are pre-filled with a volume of biologically compatible fluid.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A method for breast implantation comprising:
    inserting a breast implant through an incision in a breast of a person, the breast implant comprising:
        a major chamber having a back wall and a curved front wall, the back wall having a top end and a distal bottom end;
        a shaped chamber within an upper portion of the major chamber, the shaped chamber having an underside surface and a curved outer surface, the underside surface having a top end and a distal bottom end, a top end of the shaped chamber hingedly connected to a top end of the major chamber;

at least two piston chambers within the major chamber, a first end of each of the at least two piston chambers affixed to the distal bottom end of the back wall and a distal second end of each of the at least two piston chambers affixed to the distal bottom end of the underside surface of the shaped chamber; and a major chamber valve interfaced to the major chamber, the major chamber valve provided to insert a biologically compatible fluid into the major chamber;

a shaped chamber valve interfaced to the shaped chamber, the shaped chamber valve provided to insert the biologically compatible fluid into the shaped chamber;

a plurality of piston valves, each piston valve interfaced to one of the piston chambers, the piston valves provided to insert the biologically compatible fluid into the piston chambers;

positioning the breast implant within the breast such that the top end of the back wall is closest to a head of the person;

inserting the biologically compatible fluid into the major chamber through the major chamber valve and inserting the biologically compatible fluid into the shaped chamber through the shaped chamber valve; and independently inserting the biologically compatible fluid into each of the at least two piston chambers through the piston valves.

2. The method for breast implantation of claim 1, wherein the step of inserting the biologically compatible fluid into the at least two piston chambers includes inserting a greater amount of the biologically compatible fluid into a first of the at least two piston chambers than the amount of biologically compatible fluid in a second of the at least two piston chambers, thereby adjusting a lateral leaning of the breast implant.

3. The method for breast implantation of claim 1, wherein further comprising a step of inserting more of the biologically compatible fluid into the at least two piston chambers, thereby adjusting a lift of the breast implant.

4. The method for breast implantation of claim 1, wherein the breast implant is made of silicon.

5. The method for breast implantation of claim 1, wherein the at least two pistons comprises a first piston and a second piston, a first end of the first piston affixed to a left side of the distal bottom end of the back wall and a distal second end of the first piston affixed to a left side of the distal bottom end of the underside surface of the shaped chamber, a first end of the second piston affixed to a right side of the distal bottom end of the back wall and a distal second end of the second piston affixed to a right side of the distal bottom end of the underside surface of the shaped chamber, wherein the step of inserting the biologically compatible fluid into each of the at least two piston chambers includes inserting more of the biologically compatible fluid into the first piston to point the breast implant toward the right and inserting more of the biologically compatible fluid into the second piston to point the breast implant toward the left.

6. The method for breast implantation of claim 5, wherein the top end of the shaped chamber is hingedly connected to the top end of the major chamber by the shaped chamber valve.

7. The method for breast implantation of claim 1, wherein the at least two pistons comprises a first piston and a second piston, a first end of the first piston affixed to a left side of the distal bottom end of the back wall and a distal second end of the first piston affixed to a right side of the distal bottom end of the underside surface of the shaped chamber, a first end of the second piston affixed to a right side of the distal bottom end of the back wall and a distal second end of the second piston affixed to a left side of the distal bottom end of the underside surface of the shaped chamber, wherein the step of inserting the biologically compatible fluid into each of the at least two piston chambers includes inserting more of the biologically compatible fluid into the first piston to point the breast implant toward the left and inserting more of the biologically compatible fluid into the second piston to point the breast implant toward the right.

8. A biological prosthesis comprising:
a breast implant comprising a major chamber, the major chamber having a back wall, the back wall having a top end and a bottom end, the top end situated closest to a head of a patient into which the breast implant is installed;

a shaped chamber within the major chamber, the shaped chamber having an outwardly facing surface and an underside surface, the underside surface has a first end and a distal end, the first end of the underside surface is hingedly attached to the top end of the back wall of the major chamber;

at least two piston chambers within the major chamber, a first end of the at least two piston chambers affixed to the bottom end of the back wall and a distal end of the at least two piston chambers affixed to the distal end of the underside surface and a valve associated with each chamber for admitting a biologically compatible fluid into the each chamber with which it is associated;

whereas inflation of the at least two piston chambers pushes the shaped chamber upward and outward.

9. The biological prosthesis of claim 8, wherein the shaped chamber is in the shape of a crescent dome.

10. The biological prosthesis of claim 8, further comprising an easy-to-disconnect filling tube attached to each valve for filling the each chamber, the easy-to-disconnect filling tube removable from the breast implant.

11. The biological prosthesis of claim 8, wherein the breast implant is made of silica.

12. The biological prosthesis of claim 8, wherein the breast implant is made of silicon.

13. The biological prosthesis of claim 1, wherein the at least two piston chambers comprises a first piston chamber and a second piston chamber, a first end of the first piston chamber is attached to a left side of the distal end of the underside surface of the shaped chamber and a distal end of the first piston chamber is attached to a left side of the bottom end the back wall of the major chamber, a first end of the second piston chamber is attached to a right side of the distal end of the underside surface of the shaped chamber and a distal end of the second piston chamber is attached to a right side of the bottom end the back wall of the major chamber, thereby providing upward support and lateral adjustability to the shaped chamber.

14. The biological prosthesis of claim 13, wherein a first end of the shaped chamber is hingedly attached to a to end of the major chamber by one of the valves.

15. The biological prosthesis of claim 1, wherein the biologically compatible fluid is selected from the group consisting of saline and a soy-based solution.

16. A biological prosthesis for breast reconstruction of a person, the prosthesis comprising:
a breast implant comprising a major chamber, the major chamber having a back wall, the back wall having a top end and a distal bottom end, the top end positioned in the direction of a head of the person and the distal bottom end positioned in the direction of a waist of the person when the breast implant is implanted in the person;

a shaped chamber positioned within and towards the top end of the major chamber, the shaped chamber having a first end and a distal bottom end, the first end hingedly affixed to the top end of the back wall;

a first piston chamber within the major chamber, a first end of the first piston chamber affixed to a left side of the distal bottom end of the back wall and a distal end of the first piston chamber affixed to a left side of the distal bottom end of the shaped chamber;

a second piston chamber within the major chamber, a first end of the second piston chamber affixed to a right side of the distal bottom end of the back wall and a distal end of the second piston chamber affixed to a right side of the distal bottom end of the shaped chamber; and a major valve interfaced to the major chamber, a shaped chamber valve interfaced to the shaped chamber, a first piston valve interfaced to the first piston chamber and a second piston valve interfaced to the second piston chamber, the valves configured to admit fluid independently into the chambers;

whereas the first piston chamber pushes against the left side of the distal bottom end of the back wall of the shaped chamber responsive to insertion of fluid through the first piston valve and the second piston chamber pushes against the right side of the distal bottom end of the back wall of the shaped chamber, thereby controlling the lift and directionality of the breast implant.

17. The biological prosthesis of claim 16, wherein the shaped chamber is in the shape of a crescent dome.

18. The biological prosthesis of claim 16, wherein the breast implant is made of silica.

19. The biological prosthesis of claim 16, wherein the breast implant is made of silicon.

20. The biological prosthesis of claim 16, wherein the biologically compatible fluid is selected from the group consisting of saline and a soy-based solution.

21. A breast implant comprising:
a major chamber, the major chamber having a back wall, the back wall having a top end and a distal bottom end, the top end configured to be positioned in the direction of a head of a person and the distal bottom end configured to be positioned in the direction of a waist of the person when the breast implant is implanted in the person;

a shaped chamber, the shaped chamber having a curved outwardly facing surface and an underside surface, the underside surface has a first end and a distal end, the first end of the underside surface being hingedly attached to the top end of the back wall;

a first piston chamber within the major chamber, a first end of the first piston chamber affixed to a left side of the distal bottom end of the back wall and a distal end of the second piston chamber affixed to a left side of the distal end of the underside surface;

a second piston chamber within the major chamber, a first end of the second piston chamber affixed to a right side of the distal bottom end of the back wall and a distal end of the second piston chambers affixed to a right side of the distal end of the underside surface;

a major chamber valve interfaced to the major chamber, the major chamber valve provided to insert a biologically compatible fluid into the major chamber;

a shaped chamber valve interfaced to the shaped chamber, the shaped chamber valve provided to insert the biologically compatible fluid into the shaped chamber;

a first piston valve interfaced to the first piston chamber the first piston valve provided to insert the biologically compatible fluid into the first piston chamber; and a second piston valve interfaced to the second piston chamber the second piston valve provided to insert the biologically compatible fluid into the second piston chamber.

22. The breast implant of claim 21, wherein the shaped chamber is in the shape of a crescent dome.

23. The breast implant of claim 21, further comprising an easy-to-disconnect filling tube attached to each valve for filling the each chamber, the easy-to-disconnect filling tube removable from the breast implant.

24. The breast implant of claim 21, wherein filling of both the first piston chamber and the second piston chamber with an equal amount of the biologically compatible fluid provides upward and outward support to the shaped chamber.

25. The breast implant of claim 24, wherein filling the first piston chamber with a greater amount of the biologically compatible fluid than the second piston chamber points the breast implant towards a right side of the person.

26. The breast implant of claim 21, wherein filling the first piston chamber with a greater amount of the biologically compatible fluid than the first piston chamber points the breast implant towards a left side of the person.

* * * * *

UNITED STATES PATENT AND TRADEMARK OFFICE
CERTIFICATE OF CORRECTION

| | | |
|---|---|---|
| PATENT NO. | : 7,615,074 B2 | Page 1 of 1 |
| APPLICATION NO. | : 11/211340 | |
| DATED | : November 10, 2009 | |
| INVENTOR(S) | : Edward Carvallo | |

It is certified that error appears in the above-identified patent and that said Letters Patent is hereby corrected as shown below:

On the Title Page Item (76)
The inventor's name is listed on the published patent as Edward Carvalio. The correct spelling is Edward Carvallo.

Signed and Sealed this

Twenty-ninth Day of December, 2009

David J. Kappos
*Director of the United States Patent and Trademark Office*